United States Patent [19]

Panitz

[11] Patent Number: 4,592,894
[45] Date of Patent: Jun. 3, 1986

[54] FIELD EMISSION CHEMICAL SENSOR FOR RECEPTOR/BINDER, SUCH AS ANTIGEN/ANTIBODY

[75] Inventor: John A. Panitz, Edgewood, N. Mex.

[73] Assignee: The United States of America as represented by the United States Department of Energy, Washington, D.C.

[21] Appl. No.: 554,415

[22] Filed: Nov. 22, 1983

[51] Int. Cl.⁴ .................. H01J 1/34; H01J 1/46; G01N 33/53; G01N 33/553
[52] U.S. Cl. .................. 422/69; 250/423 F; 324/71.1; 422/68; 436/501; 436/525; 436/805; 436/806; 436/807
[58] Field of Search .............. 250/306, 423 F; 436/805, 806, 501, 525, 807; 324/71.1; 422/68, 69

[56] References Cited

U.S. PATENT DOCUMENTS

| | | |
|---|---|---|
| 3,403,081 | 9/1968 | Rohrback . |
| 3,853,467 | 10/1974 | Giaever . |
| 3,868,507 | 2/1975 | Panitz . |
| 3,966,580 | 6/1976 | Janata . |
| 4,072,576 | 2/1978 | Arwin . |
| 4,151,049 | 4/1979 | Janata . |
| 4,238,757 | 12/1980 | Schenck . |
| 4,273,636 | 6/1981 | Shimada . |
| 4,278,652 | 7/1981 | Niemann . |
| 4,508,832 | 4/1985 | Carter ..................... 436/805 X |

FOREIGN PATENT DOCUMENTS

EP27517 4/1981 European Pat. Off. .

OTHER PUBLICATIONS

Gomer, R., Accounts of Chemical Research, 5(2), 41-48 (Feb. 1972).
Kellogg, G. L. et al., Surface Science, 62(2), 343-360 (Feb. 1977).

Primary Examiner—Sidney Marantz
Attorney, Agent, or Firm—George H. Libman; Albert Sopp; Judson R. Hightower

[57] ABSTRACT

A field emission chemical sensor for specific detection of a chemical entity in a sample includes a closed chamber enclosing two field emission electrode sets, each field emission electrode set comprising (a) an electron emitter electrode from which field emission electrons can be emitted when an effective voltage is connected to the electrode set; and (b) a collector electrode which will capture said electrons emitted from said emitter electrode. One of the electrode sets is passive to the chemical entity and the other is active thereto and has an active emitter electrode which will bind the chemical entity when contacted therewith.

13 Claims, 2 Drawing Figures

FIELD EMISSION CHEMICAL SENSOR FOR RECEPTOR/BINDER, SUCH AS ANTIGEN/ANTIBODY

The U.S. Government has rights in this invention pursuant to Contract DE-AC04-76DP00789 between the U.S. Department of Energy and Western Electric Company.

BACKGROUND OF THE INVENTION

This invention relates to a new sensor and associated method for detecting the presence of specific chemical entities even at extremely low concentrations. Particularly, it is applicable to the detection of one component of a receptor/binder pair, typically an antibody/antigen pair.

Heretofore, many methods and devices have been disclosed for the detection of chemical entities such as antibodies and/or antigens. These include systems based upon a field effect transistor with a gate region modified to detect a biochemical contaminant. See, e.g., U.S. Pat. Nos. 4,238,757 and 4,273,636. Other systems detect biochemical agents based on surface changes in a hydrophobic membrane upon adsorption of an antigen (U.S. Pat. Nos. 3,966,580 and 4,151,049); changes in an electrochemical cell having one electrode which is immunochemically active (U.S. Pat. No. 3,403,081); changes in the capacitance of a system having an immunochemically active electrode (U.S. Pat. No. 4,072,576); as well as more classical methods, see, e.g., U.S. Pat. No. 4,278,652.

All of these methods are deficient from various points of view. For example, none address the often difficult problem of non-specific binding of the species of interest. This is especially exacerbating when only a low signal to noise ratio is available either due to detector insensitivity or a very low concentration of unknown species. Furthermore, many of the prior art techniques are not adaptable to liquid and gaseous samples.

SUMMARY OF THE INVENTION

Accordingly, it is an object of this invention to provide a new chemical sensor and an associated method for detecting chemical species.

It is another object of this invention to provide such a sensor and method for detecting very low concentrations of chemical species, even single molecules.

It is yet another object of this invention to provide such a sensor and method which is particularly applicable to the detection of one component of a unique receptor/binder pair, e.g., an antibody/antigen pair.

It is a further object of this invention to provide such a sensor and method which eliminates or significantly reduces non-specific binding of the species of interest.

It is an additional object of this invention to provide such a sensor and method which are based upon the field emission effect or, more generally, upon the effect of electron tunneling from a metal or semiconductor or insulator through a receptor/binding pair, into a liquid, gas or solid medium to a counter electrode of suitable composition.

Upon further study of the specification and appended claims, further objects and advantages of this invention will become apparent to those skilled in the art.

These objects have been attained by providing a field emission chemical sensor for specific detection of a single component of a receptor/binder pair contained in a liquid sample including field-electron emission and collector electrodes for contacting the sample, the emission electrode having bound to its surface one of the components, wherein the magnitude of an electrical current conducted in the sample between the electrodes is indicative of the presence of the other of the components in molecular amounts in the sample. The invention further comprises a control electrode pair with a second field-electron emission electrode having bound thereto sufficient amounts of the other component as to saturate the control pair with this material. The differential current between the control pair and the first pair of electrodes is used to determine the presence of the other component. A further refinement of the invention includes a passivating layer of material covering all metallic surfaces of the electrodes and any surrounding chamber to limit contamination of the surfaces to only the components of the receptor/binder pair. In the preferred embodiment, this pair comprises an antibody/antigen pair.

In operation, the sensor will be connected to a power supply which provides the necessary voltage across the electrodes. In a preferred mode, the field emission currents from each set of electrodes will be fed to a differential amplifier which will subtract the two currents and provide a single differential current, the latter being a convenient means of observing the detection of the unknown species.

The method of this invention involves the admission of the unknown sample into the chamber of the sensor, whereupon the species to be detected will become attached to the active electrode surface causing a detectable change in differential current.

BRIEF DESCRIPTION OF THE DRAWING

Various other objects, features and attendant advantages of the present invention will be more fully appreciated as the same becomes better understood when considered in conjunction with the accompanying drawing, and wherein.

DETAILED DISCUSSION

The Field-Electron Emission Effect

Figure 1:
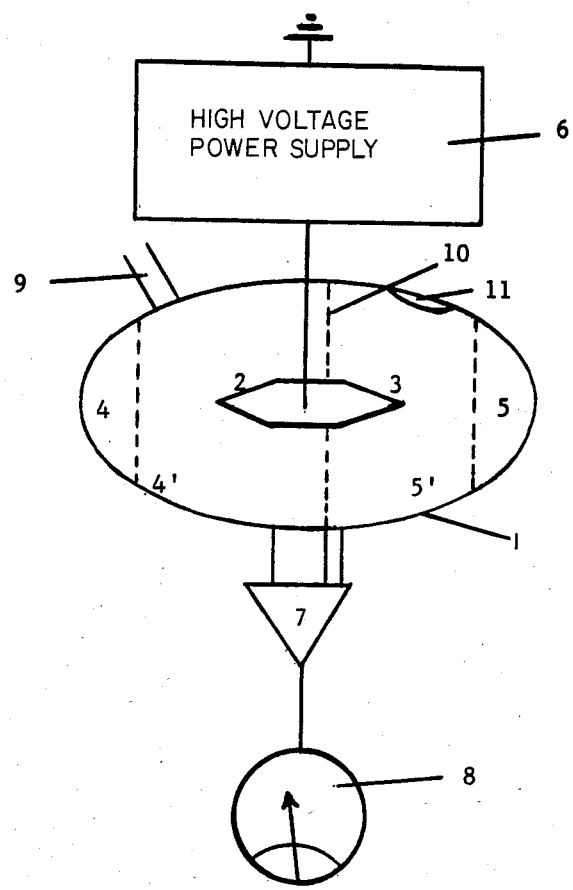
FIG. 1 shows one embodiment of the sensor of this invention.

This invention is based upon the field-emission effect wherein electrons tunnel through the potential barrier at a metal's surface into vacuum, a gas or a liquid in response to an applied voltage. The effect is so sensitive that contamination of the surface by even a single adsorbed atom (adatom) will affect the current derived from the flow of field emission electrons. Such current effects can be used to detect the presence of the adatom on the surface. The following discussion is given to aid in the understanding of this application.

The Field-Electron Emission Diode

A conventional field-electron emission diode comprises a sharply pointed wire cathode placed in vacuum opposite a planar anode. The cathode is prepared by electrochemical polishing techniques. Thermal annealing in vacuum produces a multifaceted apex whose shape is approximately hemispherical. Since the size of the tip apex is much smaller than the size of the individual crystallites in the polycrystalline wire from which it is etched, the tip apex is normally formed from a single perfect crystal. (Occasionaly, a tip will be etched from two or more single crystallites of a polycrystalline wire, separated by well defined grain boundaries.) The etching process exposes at the surface of the tip apex many different crystal planes of low and high Miller indices, smoothly joined into an approximately hemispherical contour. Since individual crystal planes have different packing densities of atoms, they produce inherently different charge distributions on the surface. As a result, the distribution of charge density on a clean tip surface will strongly depend on the local crystallography of the surface and will lead to significant variations in the tunneling probability of electrons over the surface.

If the tip is biased to a suitable negative potential, and placed opposite a fluorescing anode, an image which maps field-electron emission probability over the tip surface will be observed. Since the field-emitted electrons will follow almost radially diverging electric field lines from the tip surface, the image will be magnified hundreds of thousands of times. The resolution of the image is typically better than two nanometers. This means that variations in the surface charge density or "work-function," can be observed on a nanometer scale. Adsorption on the surface will tend to change the distribution of surface charge density. If the resulting change in work function is sufficient, the adsorbate will become visible in the field-emission pattern as a localized contrast variation.

See, e.g., W. P. Dyke et al, *Advances in Electronics and Electron Physics*, ed. L. Marton 8 (John Wiley, New York, 1956) and R. Gomer, *Field Emission Harvard University Press*, Cambridge, MA, 1961.

The simplicity of this technique allowed Müller to study adsorption and desorption phenomena on clean metal surfaces in ultra-high vacuum as early as 1937. In 1950, Müller detected the adsorption of individual organic molecules deposited from the vapor phase onto a clean tip surface. Although the resulting images clearly demonstrated the adsorption of a single molecule, they did not reflect the molecule's known shape. The presence of a single molecule could be detected, but its morphology could not be reliably imaged.

Although the vacuum field-emission diode can detect the presence of individual, organic molecules, it is not an ideal detector for a chemical sensor. Its major drawback is the requirement that ultra-high vacuum conditions be maintained. Ultra-high vacuum avoids the problem of tip contamination from ambient gas molecules, and provides an adequate mean free path for the imaging electrons.

If the imaging criteria are relaxed, it is feasible to initiate field-emission within a totally liquid environment, R. Gomer, Accounts of Chem. Res. 5, 41 (1972), whose entire disclosure is incorporated by reference herein. Provided electron mobilities are high enough to prevent space charge (at least at low currents), and energy losing collisions are efficient (so that field-emitted electrons never acquire enough energy to ionize atoms or molecules in the liquid), a linear current-voltage characteristic can be obtained.

The Fowler-Nordheim Equation

In order for an electron to tunnel from a metal into vacuum it must acquire sufficient energy to overcome the potential barrier at the surface presented by the work function $\phi$. Classically, the electron must be activated over the work function barrier. However, in the presence of a sufficiently large electric field, the barrier will be distorted and the probability for electron tunneling directly through the barrier will become significant. Field emission of electrons at room temperature (where direct thermal activation over the barrier can be neglected) is a direct manifestation of quantum mechanical tunneling, and as such has no classical analog.

The theoretical expression which predicts the current-voltage relation in a vacuum field-emission diode was derived by Fowler and Nordheim in 1928. In addition to the assumption of a classical image potential several other simplifying assumptions were made. They included:

1. the assumption that the metal behaves as though it were simple, one-dimensional, and free-electron-like. Fermi-Dirac statistics were assumed.
2. the assumption that the emitter-tip surface can be approximated as a smooth, infinite plane where surface irregularities are always much smaller than the spatial extent of the potential barrier.
3. the assumption that the work function, $\phi$, is uniform and isotropic over the emitter tip surface.

Under these assumptions, if the barrier penetration probability is calculated from the WKB approximation and multiplied by the arrival rate of electrons at the barrier, the current density (in amps per $cm^2$) is the Fowler-Nordheim equation:

$$J = I/A = 1.54 \times 10^{-6} \exp[-6.83 \times 10^7 e^{3/2} \phi^{3/2} f(y)/F] e \phi t^2(y) \quad (1)$$

where A is the emitting area of the tip, t(y) and f(y) are tabulated functions of $y = (eF)^{\frac{1}{2}}/\phi$ and, in vacuum, the electric field strength is given by:

$$F = V/kR \quad (2)$$

R is the emitter-tip radius and k is a proportionality constant which depends on the exact cathode-anode geometry (for an isolated sphere in space k=1). Since a field of strength of a few tenths of a volt per angstrom is required in order to observe a field emission current, a potential of the order of several kilovolts must be applied to a typical field-emitter tip having an apex radius of curvature of a few thousand angstroms.

If the logarithm of $I/V^2$ is plotted against $I/V$, a straight line is obtained. This is the Fowler-Nordheim characteristic which identifies field-emission in the absence of space charge. If space charge occurs, the plot will deviate from linearity at large values of V. From the Fowler-Nordheim equation, the slope of the straight line is found to be:

$$S = -6.8 \times 10^7 e^{3/2} \phi^{3/2} f(y) KR \quad (3)$$

Since an average work function for the clean metal surface is usually known, KR can be uniquely determined for a given cathode-anode geometry.

If the vacuum diode is filled with a suitable liquid, the potential distribution will be unchanged, Gomer (1972), supra. If KR has been measured in vacuum, the electric field can be determined from equation (2) realizing that the potential to achieve a given field strength will be reduced by the dielectric constant of the liquid. The molecules of the liquid will tend to dwell or adsorb onto the tip surface. Although the work function of the surface will differ from its vacuum value, it will approach an equilibrium value with short, temporal fluctuations indicating the adsorption and desorption of liquid phase species.

Prior Single Atom Detection

Using changes in the Fowler-Nordheim characteristics, single atom adsorption can be detected in a vacuum environment by monitoring changes in field-emission current, see e.g., G. L. Kellogg et al, Surf. Sci. 62, 343 (1977) whose entire disclosure is incorporated by reference herein. In order to establish this level of detection capability, the tip surface can be imaged in atomic resolution by field-ion microscopy. Consequently, individual adsorption events can be observed and correlated with the change in field-emission current which they produce. Since the high electric field strength required for field-ion imaging ($>2V/\text{Å}$) will desorb or destroy organic molecules present on the tip surface, only metal atom adsorption could be observed using this known method.

Kellogg et al., demonstrated the sensitivity of the field-emission current to single atom adsorption on a field emitter tip. Tungsten atoms were evaporated from a heated filament and allowed to adsorb on a tungsten field-emitter tip in high vacuum. The field-emission current showed two distinct changes in level. These changes, of equal height, corresponded to the adsorption of two metal atoms onto the tip surface. This was confirmed by field-ion imaging after the adsorption event.

The Liquid Field Emission Detector

A schematic representation of a sensor of this invention is shown in FIG. 1. A chamber (1) houses two electrode sets. Each set has a field-electron emitter (e.g. cathode) electrode, hereinafter called an emitter electrode (2,3) and a collector (e.g. anode) elctrode (4,5,4',5',). The emitter electrode will emit electrons (i.e., via the tunneling phenomenon) which, in turn, will be captured by the collector electrode when the electrodes are activated by a conventional low current, high voltage power supply (6). The emitter electrodes can have the fully conventional field emission tip configuration, i.e., that of a wire or rod having a pointed tip (e.g., radii of about 40-400 nm). Alternately, an array of emitter tips produced by conventional semiconductor fabrication techniques can be employed in order to increase the active area of the diode and its sensitivity. The collector may be a curved surface which is concave (4,5) with respect to the tip in order to facilitate collection of emitted electrons. Of course, planar electrode collectors (4',5') can also be utilized.

Figure 2:
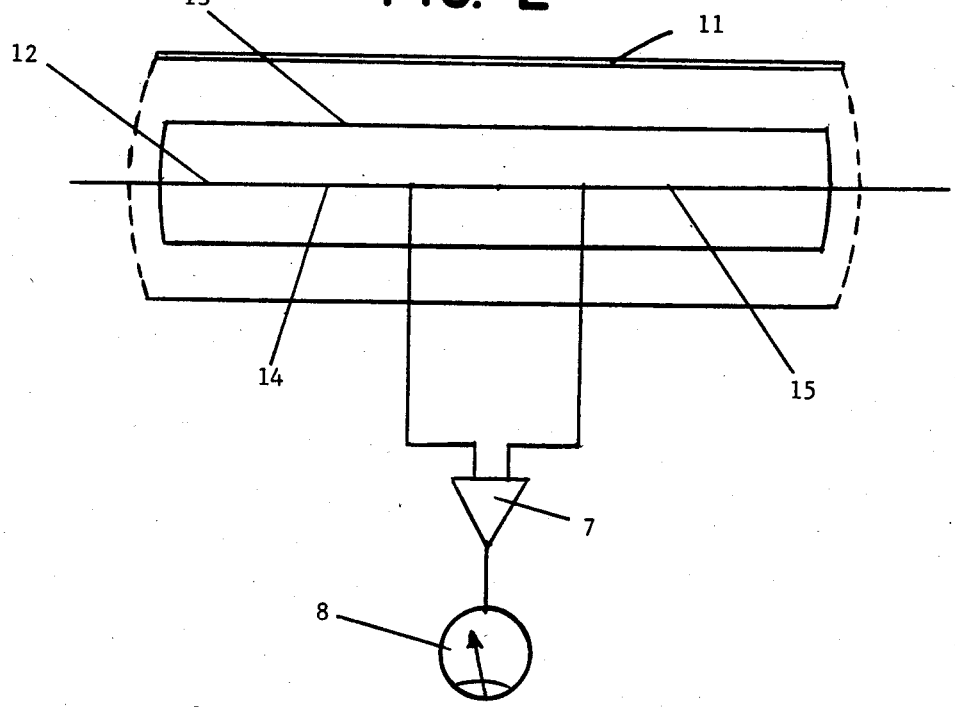
FIG. 2 shows an alternative electrode configuration.

In another preferred electrode pair configuration, the emitter is a wire (12) and is surrounded by a cylindrical collector electrode (13), the emitter electrode being located at the longitudinal axis of the cylinder as depicted in FIG. 2. In this configuration, much smaller spacings between the electrodes can be attained, in principle, up to a distance just short of electrical shorting. As will be clear from the following, the shorter the distance, the more efficient is the detection system. In a preferred configuration, one portion (14) (e.g., one-half) of the wire emitter is passivated in accordance with the following discussion and forms the passive electrode, while the remainder (15) is active (also see the following) and forms the active electrode. The cylinder is separated into two correspondingly configured regions.

In any configuration, the electrodes can be fabricated from any conductive or semiconducting material which permits the passivation and adsorption treatments described in detail below. Since electrode surfaces will be coated with adsorbed layers of material, preferred electrodes will be those which enable the achievement of the most complete and most uniform surface coverage, typically with proteinaceous material. Thus, electrode surfaces which enable efficient and complete immobilization of proteins will be preferred. Suitable electrode materials include those which are conventional for field emission tips such as tungsten, iridium, gold, platinum, etc. and, as well, semiconducting electrodes and electrodes which have oxide surfaces, e.g., tungsten oxide, molybdenum oxide, nickle oxide and silicon having silicon dioxide surface sites. Such oxide layers generally provide useful bonding sites for proteinaceous molecules such as antibodies and/or antigens, e.g., via OH groups bonded to the surfaces. Of course, as further discussed below, any means of attaching proteinaceous materials to these surfaces is included within the scope of this invention including surface activation by chemical treatment or preadsorption or postadsorption of a suitable adherent.

All aspects of the power supply amplification, circuitry, metering, etc. associated with the sensor and method of this invention are fully conventional, as are its operating characteristics and settings. The commercially readily available equipment is that which is commonly used in low current, high impedance systems. In essence, a fully conventional power supply (6) providing the conventional voltages necessary to achieve field emission effects will be attached to the two electrode pairs. The current caused by the flow of electrons from the emitter to the collector will preferably be passed into a fully conventional differential amplifier (7) which will subtract the two currents and provide a differential current readout which can be passed to conventional device (8), e.g., meters, data processing equipment, etc. This current is directly related to differences between the two emitter surfaces as explained more fully below.

A key aspect of this invention involves the use of a control electrode pair which does not respond to the chemical entity being detected and one electrode pair which is active due to this chemical species. That is, once the unknown sample is admitted into the region of the two electrode pairs, it will have no effect upon one of the electrodes but can only affect the other active electrode. This configuration is achieved by inactivating one electrode and activating the other.

For detection of antibodies or antigens, both passification and activation will typically be accomplished by fully conventional protein adsorption techniques, e.g., as described in U.S. Pat. No. 3,853,467; F. A. Ward, *A Primer of Immunology* (Butterworth, London, 1970) whose disclosures are being incorporated by reference herein, as well as in many other texts. See also, Panitz et al., Surf. Sci. 97, 25 (1980); Panitz, J. Micros. (GB) 125, 1(1982); and Panitz et al., Ultramicroscopy 6, 3(1981), all of whose disclosures are incorporated by reference herein, for additional information specifically regarding the binding of protein to electrode surfaces. These disclose adsorption of monolayers of protein onto tungsten field-emitter tips from aqueous solution and include the use of the immunological reaction. Transmission electron microscope (TEM) images of a tungsten tip exposed first to a solution of Bovine Serum Albumin (BSA) and then to a solution of anti-BSA rabbit serum containing BSA specific antibodies, $Ab_1$, of the IgG type were taken. The effect on these images of an additional exposure to a solution of antirabbit goat serum containing $Ab_1$ specific antibodies $Ab_2$, was determined. In both cases, the layer thicknesses were in agreement with those obtained from other more inexact measurements, and were consistent with the size of the BSA and antibody molecules. The specificity of the immunological reactions on the tip surface was verified by first exposing the tip to BSA and then to $Ab_2$. No layer build-up was observed in the TEM. Similarly, no build-up was observed by exposing a BSA-$Ab_1$-$Ab_2$ layer to $Ab_1$. In these experiments, the tip was not allowed to dry between successive antibody exposures. However, since active antisera was made from commercial lyophilized powder, drying (and even vacuum dessioation) would not destroy the immunological response of a deposited antibody layer. Thus, a choice can be made between deposition accomplished in situ wherein the aqueous deposition medium is gradually replaced with a working fluid more suitable for the field emission effect, or drying must take place.

These protein deposition results are important because of the desirability of using immunological reactions to cover all interior surfaces of the detector with a passivating layer of protein. Since an antigenic species will bind to either a metal surface or its specific antibody, all free surface sites are preferably blocked. The most difficult surface to passivate is the highly curved apex of the field emitter tip where surface tension forces during drying can alter layer morphology. It has been shown that unstained protein monolayers on a field-emitter tip tend to be incomplete. However, the same imaging experiments (which were nondestructive) also demonstrated that tips covered with such protein could be cycled between ambient atmosphere and vacuum without changing the protein distribution on their apex. Thus, saturation coverage which was very stable could readily be achieved.

For example, control passivation or blocking can be achieved by reacting a proteinaceous substance with the surface to be passivated or blocked for a sufficient length of time to adsorb onto the surface an essentially saturation amount of the protein. Any readily available proteinaceous material can be used, as is fully conventional. Where possible, the antibody(antigen) to the antigen(antibody) being detected can be directly adsorbed onto the surface to be passivated. In other cases, an intermediate protein can first be adsorbed onto the surface and then the antibody or antigen can be coupled thereto. Control is achieved by saturation of the surface with antibody(antigen) so that when the sample containing the unknown antibody (antigen) is contacted therewith, no binding will be possible.

Of course, any other passivation technique can also be employed. The important feature is the inability of the passivated surface to bind with the unknown antibody or antigen. To the extent possible, 100% coverage of the surface to be passivated will be achieved. However, in cases where this is not practically realizable, as long as the surface has been saturated with the component to be detected, further adsorption of this component during the detection operation will be statistically negligible.

Activation of the active electrode takes place using much the same process. That is, the antibody to the antigen to be detected or, conversely, the antigen to the antibody to be detected, is directly coupled to the electrode surface to the maximum extent possible or is coupled thereto via an intermediate, more readily adsorbable protein or by suitable chemical modification of the surface. It is further preferred that only the active tip of the active electrode be activated in order to eliminate or significantly lessen the chances that the chemical species to be detected will become bound to a portion of the electrode from which field emission electrons will not be emitted. (See example 1 herein.)

The differential current provided by the passivated electrode and the activated electrode prior to use in detecting an unknown species will be one which is highly stable and reproducible over a wide range of voltage/current combinations. One or more such stable configurations (determinable routinely, perhaps with a few routine preliminary experiments), can be chosen as a baseline for the sensor prior to contact with the unknown sample. Upon binding of the species to be detected to the active surface, readily observable changes in this otherwise stable differential current will occur, indicating the presence of the species to be detected. Accordingly, it is not necessary to perform a Fowler/Nordheim analysis as described in the preceding in order to establish the presence of the unknown chemical entity in the sensor. Because of the unique stability and reproducibility achieved by this invention, only simple detection of current level changes is necessary. For most systems, there will be a routinely determinable correlation between the current changes and the concentration of the unknown species thereby providing a convenient quantitative or semi-quantitative means of determining not only the presence of an unknown species but also its concentration.

The limit of detectability of the sensor of this invention is as low as a single molecule or a few molecules of the unknown species for the configuration wherein all surfaces of the sensor have been passivated except for the active electrode tip. The upper limit on sensor detectability is set only by the active surface area. Hence, a rather broad range can be provided in accordance with particular application system requirements. For example, using the electrode pair comprising an emitter wire surrounded by a collector cylinder, relatively large surface areas can be achieved. Even within the given dimensions of one such wire/cylinder set, the surface area can be varied, e.g., by varying the percentage of the wire which is bound to passivating protein versus that which is bound to activating protein.

The interior volume of the chamber of the sensor can be filled with any of a variety of liquids or gases. While the chemical species is being detected, the inside environment of the chamber must be compatible with the binding of the unknown species to the active electrode surface. Once this step of the detection has been accomplished, the adsorption-compatible liquid can be replaced with a liquid which is compatible with the measurement of the field emission current, e.g., using conventional methods such as slow continuous exchange of the former liquid by the latter liquid or by conventional critical point drying of the chamber after the binding of the antibody and antigen followed by filling with a suitable dielectric liquid enabling field emission current determinations. Because of the stability and reproducibility of the sensor of this invention, it will generally not be necessary to precede this sequence by a prior exchange of dielectric liquid with liquid which is compatible with chemical species binding. That is, after fabrication of a sensor of this invention in accordance with predetermined specifications determined in accordance with the foregoing, it will not be necessary in each case to perform an actual baseline measurement of field emission current using a compatible dielectric liquid. Rather, a reliable baseline current will be known from preliminary experiments, thereby obviating the necessity of replacing dielectric liquid with e.g., antibody/antigen binding compatible environments.

In a preferred version of the sensor and method of this invention, the detector is filled with a liquid which is compatible both with the field emission current and with the binding of the chemical species to the active emitter tip. Such suitable liquids include binary mixtures of dimethylsulfoxide and water or of sugar and water, e.g., 20–60%, preferably about 30% concentrations of DMSO in water. It is important that all of the working fluids employed in conjunction with this invention be of high purity. For example, DMSO packed under pure nitrogen in sealed glass ampules and 18 Megohm, semiconductor grade, double distilled water have given satisfactory results.

This invention is applicable to the detection of a component of a receptor/binder pair wherein the receptor uniquely binds with the binder and vice versa. Typically, these will be components of antibody/antigen pairs including large molecular weight components wherein both are proteins and also pairs wherein the antigen is a small molecule such as a hapten. The latter embodiment is particularly of interest where detection of small molecules is important e.g., where it is desired to detect and identify low levels of carcinogens, chemical warfare agents, etc. Antigens, including haptens, can be detected in both gaseous or liquid unknown samples. For example, gases can be admitted into the chamber in any conventional fashion using conventional input means (9, FIG. 1), and, e.g., bubbled through the sensor. Liquids can also be added to the sensor interior in any conventional fashion. As noted above, the system of this invention can be adapted to the detection of either the antigen or the antibody of an antigen/antibody pair.

In a preferred embodiment of the sensor of this invention, the detector is provided with a white light source 11 (e.g., a high pressure mercury arc) containing radiation of wavelengths in the near U.V. and visible ranges. This source will be positioned such that the light is focused on the emitter electrodes using conventional optics, e.g., quartz or sapphire windows in the chamber body in association with lenses made of the same or similar material by which the light can be directed and focused onto the emitter. Alternatively, in the cyclindrical electrode configuration, a conventional, cylindrical concentrating reflector can be positioned about the electrode to provide the necessary illumination, e.g., in conjunction with a light permeable cyclindrical collecting electrode. Energy transfer from the radiation to the electrode will enhance the emission of the field emission electrons. Thus, for example, in one mode of operation, the voltage across the electrodes can be set at a level which is insufficient to cause field emission of electrons. Upon pulsing of the light source, however, the resultant enhancement will cause sufficient electron F- emission to provide a measurable current. Thus, pulsing of the light source provides a means for operating the detector in a pulse mode. Alternatively, the light source can simply be used to enhance the level of current.

In another embodiment of this invention, a semipermeable membrane or other suitable filter can be included in the chamber, e.g., in the sample entry port (9). This can be conventionally designed to filter out molecules having sizes which are of a completely different range from that undergoing investigation. Suitable semi-permeable membranes are sold under the commercial name Nuclepore. Of course, any other means for separating out molecular species which are not to be detected can also be employed in conjunction with the sensor of this invention.

This invention is not limited to sensors having a passive reference electrode set and a single active electrode set. Rather, any number of active electrodes can be included in a sensor. For example, a single sensor can incorporate several active electrode pairs, each one being active with respect to a different chemical species. The passive reference electrode pair and all other internal surfaces of the sensor which can come in contact with the unknown sample will be passivated in accordance with the foregoing such that nonspecific binding to such surfaces by the species to be detected will be eliminated or greatly minimized. It is further possible for the chamber of the sensor to have two or more separate compartments e.g., one housing the passive electrode and the other the active electrode(s). See optional component (10) in FIG. 1.

It is even possible for the sensor of this invention to comprise only the active electrode set. Because of the stability and reproducibility of the system, a change in the current level from this single electrode set will be indicative of the detection of the unknown species in accordance with the foregoing. The dual passive/active electrode configuration is preferred, however, to minimize spurious changes in current.

Because the sensors of this invention are so economical, it will normally not be necessary to renew the detector once the active tip of the emitter has been saturated. However, where it is feasible to do so, conventional controlled field desorption of the adsorbed layers can be accomplished followed by reactivation thereof in accordance with the foregoing. Regarding desorption, see, e.g., Panitz, Ultramicroscopy 1, 3 (1982) whose disclosure is incorporated by reference herein.

In yet another preferred version of this invention, the active emitter tip, after being coated with the active antibody or antigen component, will be covered with a protective membrane layer, e.g., a phospholipid layer or other monomolecular film layer having the necessary properties described above for the media of the chamber, e.g., using the conventional Langmuir/Blodgett technique. See, e.g., Blodgett, J. Am. Chem. Soc. 57, 1007 (1937). Such membrane layers can be used to seal a liquid medium onto the tip, e.g., conventional physiologically acceptable media in which the antibody/antigen reaction can occur, e.g., sugar water layers, etc. At the same time, these layers will permit transfer of emitted electrons to the collector electrode which may be deposited as a conducting material directly onto the membrane surface. The phase in the interior of the chamber can be one of the liquid phases mentioned above or, more preferably can be an inert gas which has a high ionization potential and thereby greatly minimizes ionization by the emitted electrons and, at the same time, has a lesser tendency to denature either the antibodies or antigens involved. Since antibodies can be made mobile in conjunction with such monomolecular layer film formation, these techniques can also enhance homogeneity and percent saturation of active antibody or antigen on the surface tip. Of course, such monomolecular film layers can themselves be used as passivating layers to which, optionally, can be bound other active species.

When low levels of unknown species are to be detected, the sampling times necessary for the species to reach the activated tip can be unacceptable for certain applications, e.g., due to a relatively large chamber volume. In this case, the migration of the species to the active surface can be enhanced by decreasing the chamber volume (e.g., by using the cylindrical electrode configuration mentioned above wherein small openings are facilitated) or by providing a bias field at the active surface using fully conventional electronic circuitry. This field is analogous to the electrophoresis fields used in many biochemical operations to cause migration of biological macromolecules such as antibodies and/or antigens. Here, the bias field will enhance the migration of the unknown antigen or antibody to the active site only, thereby significantly decreasing the necessary sampling time. Detection of low levels of the unknown can also be enhanced, by employing full passivation of all surfaces except for the active tip (to enhance detector sensitivity and eliminate or lessen non-specific events); or by employing the wire/cylinder electrode combination or arrays of field-emitter tips simply because of the increased active surface area which these provide.

The sensor and method of this invention are advantageous from many points of view. The sensor is small, of low weight, has a low power consumption in the microwatt range, is relatively insensitive to temperature variations and vibrations and is nondestructive with respect to the unknown species. It can be operated remotely in continuous or pulsed fashion. Its presence is also very difficult to detect since it emits no radiation. Furthermore, it is so inexpensive that once the detector becomes saturated, it can be readily discarded and replaced with a new sensor.

The details of the method of this invention are clear from the foregoing discussion. When using a chamber liquid which is compatible with both the field emission of electrons and the interaction of the unknown chemical species with the active surface, it is simply necessary to pass the unknown sample into the detector. A change in the steady state current will be indicative of the detection of the specific chemical species for which the detector has been designed.

In another mode of operation, a sensor of this invention is designed and built. Output current characteristics are determined. These will remain reproducible and stable. Detection of an unknown simply involves filling the sensor chamber with a liquid which is compatible with the binding of the unknown species to the active emitter surface and placement thereof in the location of interest. To determine whether a detection of the unknown species has occurred, the fluid in the chamber is changed to one which is compatible with the field emission of electrons in accordance with the foregoing discussion. Subsequent measurement of a current which is different from the reproducible and stable baseline current will be indicative of the detection of the unknown chemical species of interest.

Liquids which are suitable for use in this invention and which are compatible with receptor/binder reactions are, of course, well known and discussed at length in basic literature relating to immunological reactions. See, e.g., the references incorporated by reference above. Characteristics necessary for a liquid to be compatible with the field emission effect are equally well known and discussed, e.g., in the Gomer reference incorporated above. In general, such a liquid must be one in which there is no breakdown due to the presence of the field electrons in a given configuration, e.g., typically involving electrode gaps in the micrometer range or smaller. Thus, typically, such suitable dielectrics will be very pure; will have low electron mobilities so that ionization will not be a problem; will have electron mobilities which, however, are large enough so that the electrons will by themselves or by multiple collisions with molecules of the liquid get to the conductor electrode; and, optionally, will have relatively low dielectric constants, e.g., in the range of about 4, so that unnecessarily high voltages can be avoided. Typical liquids include n-hexane or benzene, etc., as well as cryogenic liquids such as pure liquid hydrogen, liquid oxygen, etc., liquid inert gases, especially liquid zenon which can be liquified merely by application of a sufficiently high pressure, thereby avoiding otherwise necessary cryogenic equipment.

Unless indicated otherwise herein, all details of the device and method of this invention are conventional or routinely determinable from conventional considerations usually involved in field emission experiments, e.g., as disclosed in the several references incorporated by reference herein.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

Active antibody is deposited only on the emitter tip apex where the field-emission current originates. This is a preferred feature in an actual working detector because binding to antibody attached to the shank of the emitter tip will remove targeted molecules from the liquid without inducing a change in the measured Fowler-Nordheim characteristic or field emission current.

To locate active antibody only at the tip apex, the entire tip is exposed to a solution containing passivating protein. The tip is then placed in vacuum, and its apex is cleaned of all protein by controlled field-desorption (Panitz, Ultramicroscopy 7, 3 (1982)). The field-desorption process acts on the same region of the tip surface from which field-emission current originates. The tip is then exposed to antibody which only binds on the clean tip apex. Subsequently, the tip is exposed (for the second time) to a solution containing the passivating protein which now only binds to the region of the tip apex cleaned by the field-desorption process, thereby filling all gaps between antibodies. A final exposure to antigen results in binding of active antibody molecules only in the region of the tip surface which is probed by the field emission process.

EXAMPLE 2

The unique point-projection imaging technique discussed in the foregoing is used to determine the three-dimensional morphology of protein molecules deposited onto a field-emitter tip. This capability allows the direct observation of the results of exposing a tip surface to a solution of passivating molecules and antibody. To ensure that a passivating layer is present, the tip is first treated with a solution containing a protein, for example, BSA (bovine serum albumin) which readily binds to a metal surface. Without drying the tip, it is thoroughly rinsed and then exposed to a solution of antibody. This entity binds to the passivating layer and also to the antigen of interest. Ferritin molecules have been deposited on field-emitter tips and imaged.

EXAMPLE 3

Ferritin is deposited onto field-emitter tips in accordance with Examples 1 and 2. Its distribution on the field-emitter tip surface is determined by TEM and point-projection imaging. Its field-emission characteristic is studied in a liquid medium and compared to that of a clean tip immmersed in the same medium. In one embodiment, a cryogenic liquid is used and the results compared to those of the same liquid which is one which has already demonstrated a reproducible (and linear) Fowler-Nordheim characteristic in the prior art. Antibody specific to ferritin is then adsorbed onto the ferritin coated tip and studied by point-projection imaging. In an alternate embodiment, ferritin-antibody complex is first bound to the tip surface rather than pure antibody.

Detector sensitivity to ferritin binding on antibody covered tips is determined by injecting known concentrations of ferritin into the detector's working fluid. Changes in the current level and in the resulting Fowler-Nordheim characteristic are measured. The tip surface is imaged by point-projection microscopy to verify the exact number of ferritin molecules bound to the tip apex by the immunological reaction. In a similar fashion, a detector is designed and tested to determine the presence of other antigens or antibodies.

EXAMPLE 4

Cathode tips were prepared from polycrystalline tungsten wire by electropolishing in approximately 1 M NaOH at 2-3 VAC. Tips with radii of about 60 nm (as judged by TEM observations) were thermally annealed in a vacuum of about $10^{-9}$ Torr at a temperature of about 2000° C. for 1-2 minutes. Storage was in high vacuum until immediately prior to use.

With 60 nm radius tips, currents of about 10 nanoamperes could be drawn (in 30% DMSO/water) at a cathode potential of about 300 volts when the tips were coated with a layer of BSA. Uncoated tips led to immediate electrolysis of the working fluid and destruction of the cathode surface. Monolayers of ferritin and hemocyanin also allowed stable currents to be measured for periods of time greater than twenty minutes. Since the biological adlayers were not close packed (they contained pinholes), it is speculated that the observed eventual catastrophic failure of the diode after about thirty minutes of operation is due to breakdown in the vicinity of the pinholes.

Concentrations of DMSO between about 20% and 60% did not produce significant changes in the performance of the diode. Concentrations less than 10% led to instability, rapid electrolysis, and destruction of the cathode tip. Concentrations greater than 60% required an increase in operating bias and instability in the measured current. Operating temperatures of 0° C.-25° C. did not significantly change diode characteristics. DMSO packed under pure nitrogen in sealed glass ampules gave the best results. The water was 18 Megohm, semiconductor grade, double distilled in a pyrex distillation apparatus immediately prior to use.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A field emission chemical sensor for specific detection in a liquid sample of molecular amounts of one component of a unique receptor/binder pair, wherein said receptor is a chemical binding partner only for said binder partner, said sensor comprising:
    an active field emission electrode set comprising:
        field-electron emission electrode means for field-emission of electrons; and
        collector electrode means for capturing electrons emitted from said emission electrode;
        a surface of said emission electrode means having bound thereto only one component of said receptor/binder pair; and
    sample holding means for holding said liquid sample in simultaneous contact with both electrode means;
        wherein the magnitude of the electrical current conducted in said sample is indicative of the presence of the other component of said receptor/binder pair contained in the liquid sample.

2. The field emission chemical sensor of claim 1 further comprising:
    a control field-emission electrode set comprising:
        second field-electron emission electrode means for field-emission of electrons; and
        collector electrode means for capturing electrons emitted from said emission electrode;
        a surface of said second emission electrode means being blocked from said one component by having bound thereto the other component of said receptor/binder pair;
    said sample holding means also holding said liquid sample in simultaneous contact with both said second electrodes; and
    means for detecting the difference between the current between said active electrode set and said control electrode set.

3. The field emission chemical sensor of claim 2 wherein the emitter electrode is in the shape of a wire rod having a pointed tip which is the active surface and the collector is planar with respect to said tip.

4. The field emission chemical sensor of claim 2 wherein, in each electrode set, the emitter electrode is wire-shaped and said collector electrode is cylindrical and surrounds the emitter electrode, the wire-shaped emitter being located on the longitudinal axis of the cylinder.

5. The field emission chemical sensor of claim 2 further comprising:
    field means for providing a bias field at said active electrode sufficient to enhance migration of antibody or antigen toward said active electrode.

6. The field emission chemical sensor of claim 2 further comprising:
    means for irradiating said electrode sets with electromagnetic radiation effective to enhance field emission.

7. The field emission chemical sensor of claim 2 wherein said collector electrode of said control electrode set is distinct from said collector electrode of said active electrode set.

8. The field emission chemical sensor of claim 2 wherein said collector electrode of said control electrode set is also said collector electrode of said active electrode set.

9. The field emission chemical sensor of claim 2 wherein said receptor/binder pair is an antibody/antigen pair.

10. The field emission chemical sensor of claim 9 wherein said receptor/binder pair is an antibody/hapten pair and the device is adapted for detection of the hapten, the active emitter electrode surface having bound thereto antibody to the hapten.

11. The field emission chemical sensor of claim 2 wherein said sample holding means comprises a chamber enclosing both electrode sets, and all surfaces inside said chamber, except for the active surface of the active emitter electrode, are passivated by saturation coverage (a) with said binder when the binder component of the receptor/binder pair is to be detected, or (b) with said receptor when the receptor component is to be detected.

12. The field emission chemical sensor of claim 11 wherein the interior volume of said chamber is filled with a liquid which is compatible with the passage of field emission electrons from said emitter to said collector and is compatible with the binding of the antibody with the antigen.

13. A field emission chemical sensor for specific detection of a chemical entity in a sample, comprising:
a closed chamber;
within the chamber,
(a) an electron emitter electrode from which field emission electrons can be emitted when said electrode is connected to an effective voltage; and
(b) a collector electrode which will capture electrons emitted from said emitter electrode; sample inlet means for admitting said sample into said chamber;
the surface area of said emitter electrode from which electrons are emitted being active to said chemical entity by binding with it when contacted therewith; and all other surfaces inside said chamber to which said sample has access being passive to said chemical entity.

* * * * *